Figure 1:
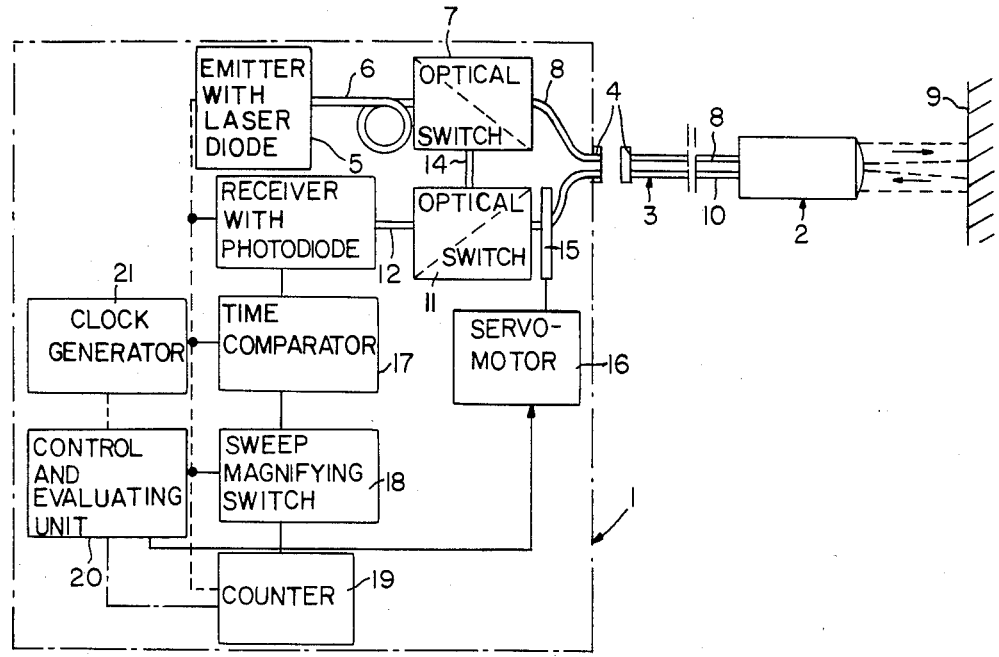

United States Patent [19]

Schwarte

[11] Patent Number: 4,737,624

[45] Date of Patent: Apr. 12, 1988

[54] OPTOELECTRIC DISTANCE MEASURING APPARATUS WITH AN OPTICAL MEASURING PROBE WITH SHARED OPTICS

[76] Inventor: Rudolf Schwarte, Kreuztaler Strasse 56, D-5902 Netphen-Dreistiefenbach, Fed. Rep. of Germany

[21] Appl. No.: 827,308

[22] PCT Filed: May 18, 1986

[86] PCT No.: PCT/EP85/00235

§ 371 Date: Jan. 22, 1986

§ 102(e) Date: Jan. 22, 1986

[87] PCT Pub. No.: WO85/05455

PCT Pub. Date: Dec. 5, 1985

[30] Foreign Application Priority Data

May 24, 1984 [DE] Fed. Rep. of Germany ....... 3419320

[51] Int. Cl.[4] .............................................. H01J 3/14
[52] U.S. Cl. .................................... 250/216; 250/227
[58] Field of Search ............... 250/227, 231 R, 231 P, 250/560, 216; 73/705; 350/96.1

[56] References Cited

U.S. PATENT DOCUMENTS

| | | | |
|---|---|---|---|
| 4,029,391 | 6/1977 | French | 250/227 |
| 4,249,076 | 2/1981 | Bergstrom et al. | 250/231 R |
| 4,325,638 | 4/1982 | Takeda et al. | 250/227 |
| 4,329,017 | 5/1982 | Kapany et al. | 250/227 |
| 4,549,504 | 6/1986 | Coursolle et al. | 73/705 |

FOREIGN PATENT DOCUMENTS

| | | |
|---|---|---|
| 0076232 | 4/1983 | European Pat. Off. . |
| 0092369 | 10/1983 | European Pat. Off. . |
| 0093437 | 11/1983 | European Pat. Off. . |
| 0135423 | 3/1985 | European Pat. Off. . |
| WO85/01117 | 3/1985 | PCT Int'l Appl. . |

*Primary Examiner*—David C. Nelms
*Attorney, Agent, or Firm*—Young & Thompson

[57] ABSTRACT

In an optoelectric distance measuring apparatus, short light pulses emitted by a laser diode are directed via a measuring probe (2) against a target object (9). The light signals reflected are collected by the measuring probe (2) and fed to a photodiode which transmits the thus-formed electric pulse signals to a control and evaluation unit. In order to make it possible to perform an accurate measurement even in the proximate area, the measuring probe (2) is provided with a double face mirror (23) extending along the optical axis of the lens (22) up to the ends of the emitting lightguide (8) and the receiving lightguide (10) which are situated approximately in the zone of the focal point. Preferably, a total-reflecting mirror in the form of two glass prisms is provided, an air gap being located between these prisms. The measuring probe (2) is made as a separate structural part and can be connected by a flexible lightguide cable to a basic unit containing the components for producing the light pulses, for transformation of the received light signals into electric pulse signals, and for the processing and evaluation of the electric pulse signals.

10 Claims, 1 Drawing Sheet

OPTOELECTRIC DISTANCE MEASURING APPARATUS WITH AN OPTICAL MEASURING PROBE WITH SHARED OPTICS

The invention relates to an optoelectric distance measuring apparatus with an optical measuring probe wherein short light pulses emitted by a laser diode are conducted via an emitting lightguide and emitted by a lens, and the light signals reflected by a target object are received and transmitted to a photodiode by way of a receiving lightguide; the photodiode feeds the thus-formed electric pulse signals to a time comparator, which latter controls the gate signals of a clock generator, the clock pulses of which are gated to a counter.

In a conventional optoelectric rangefinder, as described, for example, in the EP Publication No. 0076232, a determination is made, on the one hand, of the transit time of the light pulses (target pulses) emitted by the laser diode, reflected by a target object, and received by the photodiode and, on the other hand, of the transit time of the reference pulses emitted by the laser diode but passing by way of the optical switches and the short path to the photodiode, and evaluated for rangefinding. In this process, the first-arriving reference pulse triggers, after an optoelectric transformation in a time comparator, a gate time signal which is cut off by the later-arriving target pulse passing via the target object. During the controlled gating time, the clock pulses (150 MHz) continuously generated by a quartz oscillator are gated through to a counter. The counted pulses are fed in groups to a processor determining, by sorting and mean value formation, the distance to be detected. In the conventional measuring devices of this type, respectively a separate lens is provided for the emitting optic and receiving optic. These lenses, arranged in juxtaposition at the device, have the drawback that the light pulse, directed from the emitting lens toward an uncooperative target object is not reflected into the receiving lens at distances below about 2 m. Only at a distance of more than 2 m there begins an overlapping of the optical emitting and receiving channels, lens-shaped in cross section, but the partial overlapping existent in the proximate range leads to considerable measuring errors. These double-lens measuring devices are thus unsuitable for smaller distances. There is also the additional disadvantage that the emitting and receiving optic is located directly at the housing of the appliance, which housing also contains the components for producing the light pulses, for converting the received light signals into electric pulse signals, and for the processing and evaluation of the electric pulse signals. Considerable difficulties are also encountered due to the inhomogeneous phase front of the light pulses emitted by the laser diode and transmitted via an emitting lightguide, consisting of glass fiber, to the transmitting lens.

In contrast to the above, the invention is based on the object of fashioning an optoelectric range finder of the type described above so that a maximally accurate distance measurement is possible also at close range.

This object has been achieved according to this invention by providing the measuring probe with a double face mirror extending along the optical axis of the lens up to the ends of the emitting lightguide and receiving lightguide lying approximately in the zone of the focal point.

On account of this arrangement, the optical transmitting and receiving channels lie directly side-by-side in the lens zone, separated merely by the plane of an extremely thin mirror, so that one half of the lens is associated with the emitting channel and the other half with the receiving channel. The emitting lightguide and receiving lightguide, terminating in the zone of the focal point, permit measuring up to the lens. The optoelectric rangefinding is thus also maximally suited for level indication of tank vessels, bulk containers, and the like. Also, the edges of the emitting and receiving lobes do not overlap; rather, overlapping takes place at the location of both lobes having the broadest cross section and therefore is representative for the phase transit times. The half-lens system has the additional advantage that the change in amplitude depends only slightly on the distance in this case; this change, as compared with the conventional parallel optic, is smaller by about the factor 10.

A considerable improvement can be attained by providing that the measuring probe is equipped with a total-reflecting mirror in the form of two glass prisms, between which an air gap is present. On account of the extremely narrow air gap, the emitting and receiving channels are in optimally close proximity. Besides, the structure of the measuring probe is especially simple and compact. The compact structure of the measuring probe makes it possible to design same as a separate component connectible to a basic apparatus by means of a flexible lightguide cable, this basic apparatus containing the structural parts for producing the light pulses, for transforming the received light signals into electric pulse signals, and for the processing and evaluation of the electric pulse signals. Therefore, the measuring probe can be set up at a location other than the basic apparatus. Since no electrical components are contained in the measuring probe and in its lightguide cable, setup in explosion-endangered rooms, tank vessels, and the like is readily possible. There is also the possibility, by the use of suitable measures, to couple one or several measuring probes with a basic apparatus.

For protecting the lens, a protective tube can be arranged in front of this lens; such an arrangement may be suitable if, for example, the danger of splashing or the like consists in tank vessels. If measurement is performed only at large time intervals, then the protective tube can also be equipped with a lid, if needed, which lid is opened only during the measuring phase. Such lid can also be utilized for calibrating measurements on account of its exactly defined spacing from the optical system.

Since the measuring probe is connected to the basic device by way of a flexible lightguide cable, the probe can also be utilized for a gimbal-type mounting and can be adjusted with the aid of a servomotor in accordance with a control program. Thereby, the scanning of bulk cones in silos or scanning of contours is made possible, for example.

In order to form a homogeneous phase front of the light pulses, a precursor lightguide is suitably associated with the emitting lightguide in the basic unit for mode coupling. Respectively one optical switch for the formation of a short light path for reference signals can be located in the emitting light-guide and receiving lightguide for comparison purposes and for calibrating. It can furthermore be expedient to provide in the receiving lightguide, in front of the optical switch, an optical attenuator which is adjustable by means of a servomotor in accordance with a control program and permits adaptation to varying amplitudes of the light pulses and/or to differing distance ranges.

Figure 2:
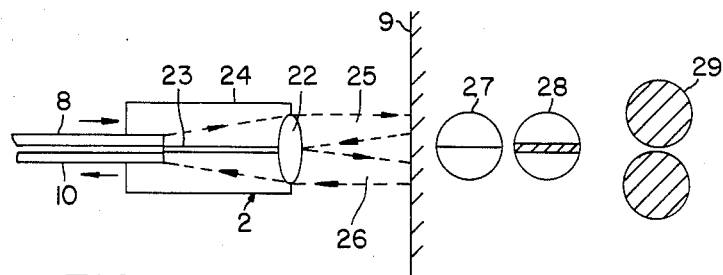
Figure 3:
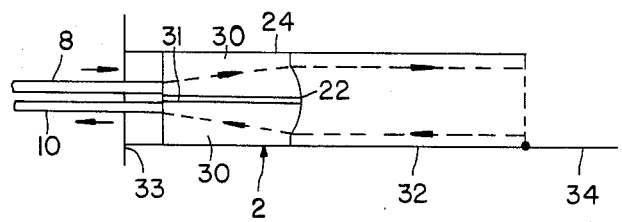

The subject matter of this invention is illustrated by way of example in the drawings wherein:

FIG. 1 shows a basic apparatus with a measuring proble coupled therewith, in a block circuit diagram, FIG. 2 shows the measuring probe of FIG. 1 in a schematic view, and FIG. 3 shows a modified measuring probe.

The optoelectric distance measuring apparatus shown in FIG. 1 consists of a basic unit 1 to which is connected a measuring probe 2 by means of a flexible lightguide cable 3 and optical coupling members 4. The basic unit 1 generates short light pulses by means of a transmitter 5 equipped with a laser diode; these light pulses are first conducted, for the purpose of mode coupling, through a precursor lightguide 6 having a length of several meters; this precursor lightguide is arranged so that it is bent into different directions, for example curved in the shape of a figure eight. For adequate coupling of the electromagnetic wave mode, the light pulses are passed through a precursor lightguide 6, for which a length of 8 meters has proved to be suitable. The light pulses pass from the precursor lightguide 6 via an optical coupler 7, the significance of which will be explained below, into the emitting lightguide 8 consisting of a section pertaining to the basic unit 1 and of a section pertaining to the flexible lightguide cable 3. The measuring probe 2 emits the light pulses toward a target object 9 and receives the reflected light signals. The received light signals are passed on, via a receiving lightguide 10, likewise made up of two sections that can be coupled together, another optical coupler 11, and a lightguide 12, to a receiver 13 equipped with a photodiode, this receiver converting the light signals into electric signals. The two above-mentioned optical couplers 7 and 11 are connected by means of at least one reference lightguide 14. Part of the light energy, about 1%, is branched off by the optical coupler 7 on the emitter side from the optical emitter channel into the reference lightguide 14 and conducted through the optical coupler 11 on the receiver side into the optical receiving channel. This branched-off light signal conducted to the receiving channel via the short path forms a reference signal received by the photodiode of the receiver 13 chronologically before the light signal (target signal) reflected by the target object, namely by the time period required for the light pulse to pass back and forth via the emitter lightguide 8, the measuring probe 2 to the target object 9 and back via the measuring probe 2 as well as the receiving lightguide 10. The transit time of the target pulse and thus the distance between the measuring probe 2 and the target object 9 can be determined from the target signal and the reference signal.

An optical attenuator 15 can be arranged, if necessary, upstream of the optical switch 11 in the receiving lightguide 10; this attenuator permits adaptation to the amplitude dynamics, and can be adjustable, for example, by means of a servomotor 16 in accordance with a control program. Instead, an electronically controllable optical attenuating member can also be utilized.

The received light signals, namely the reference and target signals, are transformed by means of the photodiode of the receiver 13 into electric pulses or signals and fed into a time comparator 17. The time comparator 17 forms gating pulses (rectangular pulses) for a counter 19 to which are gated, within the gating time, the clock pulses from a clock generator 21 (quartz oscillator). For this purpose, the gating pulses are passed over a sweep magnifying switch 18 associated, for example, with a sweep magnifying factor of 500, 1000, or the like. This sweep magnification permits exact counting of clock pulses, the frequency of which can range, for example, on the order of 50 MHz.

The thus-counted clock pulses, corresponding to the gating time, are fed to a control and evaluating unit 20 for evaluation. The clock generator 21 furthermore triggers the emitter 5 and selectively modulates the amplification of the receiver 13. Furthermore, the time comparator 17 is actuated by a time window which selects the processing of the reference signal or of the target signal; in this connection, it is possible, for example, to process in succession only reference signals or only target signals in order to form groups from these, the groups permitting evaluation by sorting and mean value formation or the like.

The measuring probe 2 shown in FIG. 2 is equipped with a lens 22 and a double face reflecting means 23, which latter extends along the optical axis of the lens 22 approximately to the focal point, in the zone of which the ends of the emitting lightguide 8 and of the receiving lightguide 10 are located side-by-side. The aforementioned components are fixedly disposed in a housing 24. By means of this arrangement, one half of the lens 22 is associated with the emitter channel 25 and the other half with the receiving channel 26. The right-hand half of FIG. 2 shows the illumination areas for various distances in front of the measuring probe. The illumination area 27 governing for the measurement forms a line directly at the lens 22. The shaded illumination area 28 applies in the proximate region, and the illumination area 29 applies in the remote region. These illumination areas, serving merely for demonstration purposes, show that the emitting and receiving channels 25, 26 overlap at the point of broadest expanse in cross section. In the remote region, the apertures of the ends of the emitting and receiving lightguides 8, 10 are depicted in the shape of a figure eight.

In the embodiment according to FIG. 3, the measuring probe 2 is provided with a total-reflecting mirror in the form of two glass prisms 30 which additionally contain the optical lens system. An air gap 31 is located between these prisms. Furthermore, it is indicated in FIG. 3 that the housing 24 of the measuring probe 2 can be extended by a protective tube 32 arranged in front of the lens 22. Flanges 33 can be provided at the housing 24 for a fixed mounting to a tank, silo, or the like. Also, the protective tube 32 can be equipped with a lid 34 adjustable, for example, by means of a servomotor (not shown) in accordance with a control program.

FIG. 1 shows that a flexible lightguide cable 3 is connected via optical coupling members 4 to the emitter and receiving lightguides 8, 10 of the basic unit 1. If necessary, it is also possible to provide several coupling sites for two or more measuring probe connections at the basic unit 1 by means of suitable optical gates or optical couplers. Another modification can be created by a gimbal-type mounting of the measuring probe 2, in which case the latter is adjustable by means of a servomotor according to a control program.

I claim:

1. In an optoelectric distance measuring apparatus comprising a laser diode for emitting short light pulses, an emitting lightguide directing said emitted light pulses toward a target, a lens disposed intermediate said emitting lightguide and a said target, a receiving lightguide receiving said light pulses reflected by a said target, a photodiode converting said received light pulses to electric pulse signals, a time comparator to which said electric pulse signals are fed, a clock generator having gate signals controlled by said time comparator and emitting clock pulses, and a counter to which said clock pulses are gated; the improvement in which said emitting and receiving lightguides terminate in distal ends disposed approximately at the focal point of said lens, and a double face reflecting means extends along the optical axis of said lens from adjacent said distal ends of said emitting and receiving lightguides to said lens, whereby a single said lens is effective to focus both said emitted and said received light pulses, without interference therebetween.

2. Optoelectric distance measuring apparatus according to claim 1, wherein said double face reflecting means is a total-reflecting mirror in the form of two glass prisms (30), between which latter an air gap (31) is provided.

3. Optoelectric distance measuring apparatus according to claim 1, wherein said emitting lightguide (8) comprises a precursor lightguide (6) for coupling of electromagnetic wave modes in said emitting lightguide, comprised by said emitted light pulses.

4. Optoelectric distance measuring apparatus according to claim 1, wherein said optical coupler (7, 11) is arranged in each of said emitting and receiving lightguides, said optical couplers being interconnected by a reference lightguide for the formation of a short light path for reference signals.

5. Optoelectric distance measuring apparatus according to claim 4, characterized in that an optical attenuator (15) is arranged in front of the optical coupler (11) in the receiving lightguide (10), this attenuator being adjustable by means of a sevomotor (16) in accordance with a control program.

6. An optical measuring probe, for use with an optoelectric distance measuring apparatus having an emitting lightguide and a receiving lightguide, comprising an emitting lightguide extension having a proximate end adapted to be detachable connected to a said emitting lightguide of a said apparatus; a receiving lightguide extension having a proximate end adapted to be detachably connected to a said receiving lightguide of a said apparatus; said emitting and receiving lightguide extensions each terminating in a respective distal end disposed within said probe; a lens disposed within said probe intermediate said respective distal ends and a target whose distance from said probe is to be measured, said distal ends being disposed approximately at the focal point of said lens; and a double face reflecting means extending along the optical axis of said lens from said respective distal ends of said emitting and receiving lightguide extensions to said lens.

7. Optical measuring probe according to claim 6, wherein said probe further comprises a tubular housing in which said distal ends, said double face reflecting means and said lens are confined.

8. Optical measuring probe according to claim 7, wherein said tubular housing extends a substantial distance beyond said lens, away from said double face reflecting means.

9. Optoelectric distance measuring apparatus according to claim 6, wherein said tubular housing (32) is equipped with a lid (34).

10. Optical measuring probe according to claim 6, wherein said measuring probe (2) is mountable on said apparatus in a gimbal-type manner and is adjustable by means of a servomotor in accordance with a control program.

* * * * *